(12) United States Patent
Stanley

(10) Patent No.: US 11,779,428 B2
(45) Date of Patent: Oct. 10, 2023

(54) DISPOSABLE MEDICAL CLAMP LIGHT

(71) Applicant: Anthony G. Stanley, North Bay Village, FL (US)

(72) Inventor: Anthony G. Stanley, North Bay Village, FL (US)

(73) Assignee: STANLEY MEDICAL DESIGNS, INC., North Bay Village, FL (US)

( * ) Notice: Subject to any disclaimer, the term of this patent is extended or adjusted under 35 U.S.C. 154(b) by 348 days.

(21) Appl. No.: 16/996,980

(22) Filed: Aug. 19, 2020

(65) Prior Publication Data

US 2021/0052346 A1 Feb. 25, 2021

Related U.S. Application Data

(60) Provisional application No. 62/890,800, filed on Aug. 23, 2019.

(51) Int. Cl.
| | | |
|---|---|---|
| *A61B 90/35* | (2016.01) | |
| *A61B 17/29* | (2006.01) | |
| *A61B 90/30* | (2016.01) | |
| *A61B 17/00* | (2006.01) | |

(52) U.S. Cl.
CPC .............. *A61B 90/35* (2016.02); *A61B 17/29* (2013.01); *A61B 2017/0023* (2013.01); *A61B 2017/00734* (2013.01); *A61B 2090/309* (2016.02)

(58) Field of Classification Search
CPC . A61B 90/35; A61B 17/29; A61B 2017/0023; A61B 2017/00734; A61B 2090/309; A61B 90/57; A61B 90/30; A61B 17/28; A61B 2017/00477
See application file for complete search history.

(56) References Cited

U.S. PATENT DOCUMENTS

| | | | | | |
|---|---|---|---|---|---|
| 2,588,288 | A | * | 3/1952 | Pohanka | A61C 1/088 439/575 |
| 5,817,119 | A | * | 10/1998 | Klieman | A61B 17/29 606/174 |
| 6,428,180 | B1 | * | 8/2002 | Karram | A61B 5/0059 362/120 |
| 6,988,814 | B1 | * | 1/2006 | Correa | B25B 9/02 362/184 |
| 8,366,441 | B2 | * | 2/2013 | Swift | A61C 19/004 433/29 |
| 8,470,260 | B2 | * | 6/2013 | Carr | F21V 33/00 422/922 |

(Continued)

*Primary Examiner* — Tsion Tumebo
(74) *Attorney, Agent, or Firm* — Dority & Manning, P.A.

(57) ABSTRACT

A disposable medical clamp light is described. The disposable medical clamp light includes a light source, a housing, and at least one attachment. The at least one attachment is configured to couple the disposable clamp light to a medical device. The at least one attachment may include an attachment clip having a first arm and a second arm extending from the housing, wherein the first arm and the second arm are configured to surround a portion of the medical device to attach the disposable clamp light to the medical device. The disposable medical clamp light may be coupled a medical device using the at least one attachment to form a lighted clamp system configured for foreign body removal from a patient. The disposable clamp light can further include a power source and a switch electrically communicating with the light source.

22 Claims, 2 Drawing Sheets

(56) References Cited

U.S. PATENT DOCUMENTS

| | | | |
|---|---|---|---|
| 2009/0097236 A1* | 4/2009 | Miller | A61B 90/30 |
| | | | 362/119 |
| 2012/0184951 A1* | 7/2012 | Viola | A61B 90/30 |
| | | | 606/34 |
| 2012/0283718 A1* | 11/2012 | Cosmescu | A61B 90/35 |
| | | | 606/41 |
| 2016/0327253 A1* | 11/2016 | Martinez | A61B 90/35 |
| 2016/0338796 A1* | 11/2016 | Cosmescu | A61B 18/1402 |
| 2018/0235444 A1* | 8/2018 | Tsai | A61B 1/303 |
| 2022/0015856 A1* | 1/2022 | Vadali | A61B 90/30 |

* cited by examiner

DISPOSABLE MEDICAL CLAMP LIGHT

RELATED APPLICATIONS

The present application claims priority to U.S. Provisional Application Ser. No. 62/890,800, filed on Aug. 23, 2019, which is incorporated herein in its entirety by reference thereto.

FIELD OF THE INVENTION

The subject matter of the present invention relates generally to a clamp light, e.g., a disposable clamp light, configured to be coupled to a medical clamp device in order to illuminate the field of view of the medical clamp device.

BACKGROUND

Foreign body removal is a common medical procedure which encompasses the removal of a foreign object from a body cavity, including the ear, nose, eye, vagina, and/or a wound. For instance, to remove a foreign body from the ear, various instruments, such as alligator forceps, curettes, plain forceps, right angle hook, balloon catheter, or lavage instrument, such as a syringe, or soft tip suction catheter, among others, may be used. Unfortunately, every individual will vary somewhat with regard to, e.g., shape, direction, and length of the ear canal, as well as location of adjacent nerves (e.g., the auricular branch of the facial nerve and the auricular branch of the vagus nerve) and other structures that could be damaged or irritated by the procedure. As such, foreign body removal procedures can require patience, dexterity, and in many cases, assistance for positioning of the ear and manipulation of the ear canal so as to alternately visualize the area and manipulate the instrument used to remove the foreign object. For instance, it can be necessary to manipulate the outer ear with one hand to modify the shape/location of the ear canal while alternately handling the foreign body removal instrument. Similar issues exist in other foreign body removal protocols in which the practitioner is attempting to both see and remove a foreign object in a small, often difficult to visualize, area.

In order to successfully remove a foreign object from a body cavity without touching or damaging sensitive body tissues as described above, proper protocols for foreign body removal require direct visualization of the body cavity with good lighting. Often, a secondary lighting source, e.g., an additional lamp, is required to supplement the light of a procedure room. For instance, the practitioner performing the foreign body removal may wear a headlamp or may require additional personnel to hold and/or adjust a floor lamp, a hand-held lamp, or other lighting source. However, these secondary lighting sources may require continual adjustment of the positioning of the lighting source due to shadows, patient movement, movement of the foreign body removal instrument within the body cavity, etc. which can increase the procedural time, thereby increasing patient discomfort. Moreover, none of these secondary lighting sources are guaranteed to directly illuminate the area surrounding the tip of the foreign body removal instrument within the body cavity in order to best visualize and remove the foreign object.

Consequently, there is a need for a light apparatus configured to be coupled to a medical clamp device or veterinary medical clamp device in order to directly illuminate the path of the clamp device. In particular, a disposable light apparatus would also be useful.

SUMMARY

The present invention is directed to a disposable medical clamp light that includes a light source, a housing, and at least one attachment. The at least one attachment is configured to couple the disposable clamp light to a medical device. The at least one attachment may include an attachment clip having a first arm and a second arm extending from the housing, wherein the first arm and the second arm are configured to surround a portion of the medical device to attach the disposable clamp light to the medical device. The disposable clamp light can further include a power source and a switch electrically communicating with the light source. The power source can optionally be a battery, such as a disposable button-type battery. The switch can optionally be a single-use switch or a multi-use switch.

The present invention is further directed to a lighted clamp system that includes a clamp configured for foreign body removal from a patient and a disposable clamp light. The disposable clamp light includes a housing, a light source, and at least one attachment. The at least one attachment secures the disposable clamp light to the clamp.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
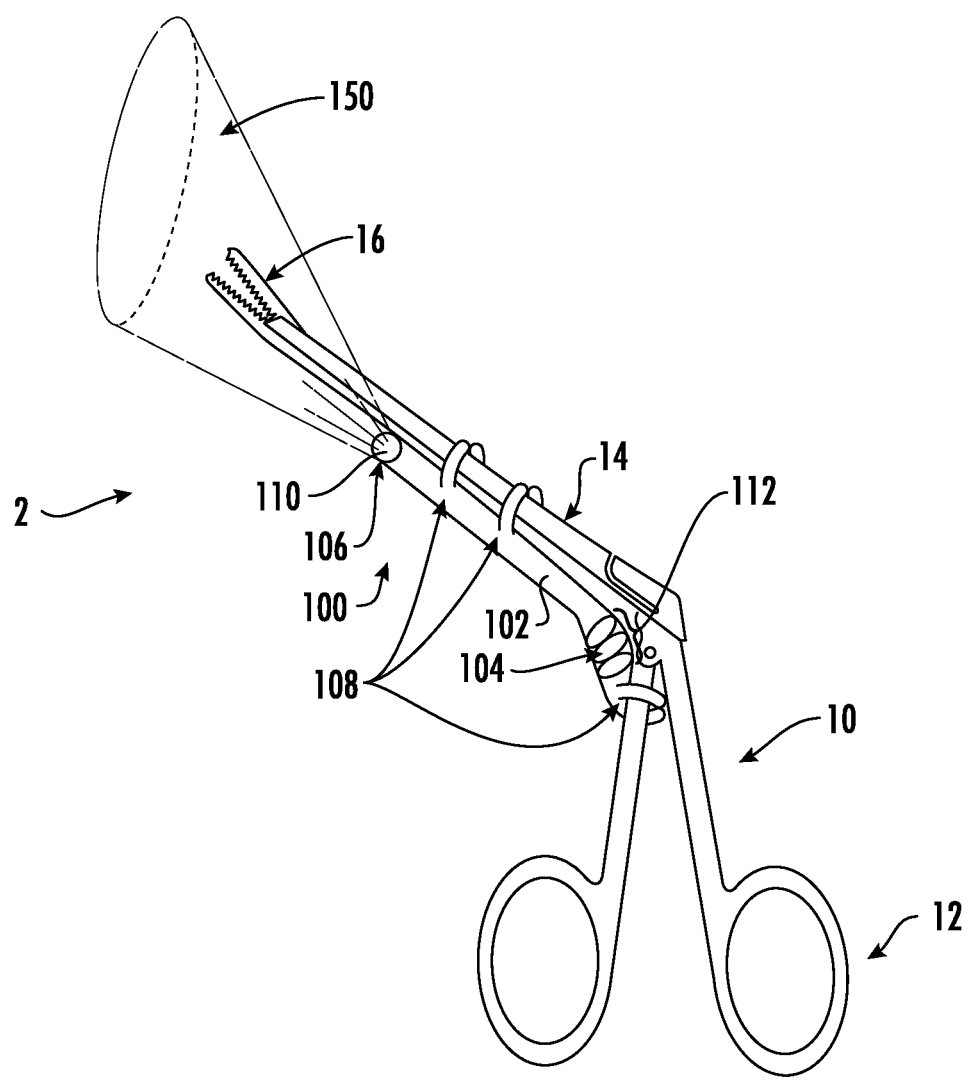
FIG. 1 illustrates a perspective view of a lighted medical clamp assembly, including a clamp light of the present invention coupled to a medical clamp device, according to one particular embodiment of the present invention.

Reference will now be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally speaking, the present invention is directed to a disposable medical clamp light and a lighted clamp system.

The disposable medical clamp light includes a light source, a housing, and at least one attachment. The at least one attachment is configured to couple the disposable clamp light to a medical device. The at least one attachment may include an attachment clip having a first arm and a second arm extending from the housing, wherein the first arm and the second arm are configured to surround a portion of the medical device to attach the disposable clamp light to the medical device. The disposable clamp light can further include a power source and a switch electrically communicating with the light source. The power source can optionally be a battery, such as a disposable button-type battery. The switch can optionally be a single-use switch or a multi-use switch. In addition, the lighted clamp system of the present invention includes the disposable clamp light coupled to a medical device, such as a medical clamp, which can be particularly useful for foreign body removal procedures. Through use of the disposable medical clamp light or lighted clamp system of the present invention, e.g., for foreign body removal, a practitioner can have a free hand for manipulation of the area to be evaluated or can use the free hand for carrying another device, e.g., a magnifying glass or the like. The disposable medical clamp light or lighted clamp system of the present invention can further be used in veterinary medical applications. Disclosed devices can provide benefit to the art, such as by preventing accidental trauma and irritation to a patient as has been known to happen previously due to an inability to visualize an area clearly during a procedure such as foreign body removal. Disclosed devices can also save time and money for a practitioner, as the single operator use of the device can remove the necessity for a second practitioner to be present to assist with positioning of a light for a procedure. The specific features of the clamp light device and system of the present invention may be better understood with reference to FIGS. 1-4.

Referring now to FIG. 1, one embodiment of a lighted clamp system 2 including a medical clamp device 10 and a clamp light 100 of the present invention are shown. As illustrated, the medical clamp device 10 includes a handle portion 12, an elongated body 14, and at least one clamp 16. An angle, e.g., an obtuse angle, may be formed between the handle 12 and the elongated body 14. For instance, as shown in FIG. 1, the medical clamp device 10 may be a standard alligator clamp or alligator forceps, sometimes known as Hartmann alligator forceps, having two jaws configured to form a clamp for removing a foreign body from a patient. However, as contemplated by the present invention, the medical clamp device 10 may be any suitable medical clamp device having a handle portion, an elongated body, and at least one clamp. It is to be understood that medical clamp devices as contemplated by the present invention may have a variety of lengths of the elongated portion 14, angles between the elongated portion 14 and the handle 12, and clamp structures (e.g., serrated or non-serrated jaws). The medical clamp device 10 can be formed of any suitable medical grade material. In general, the medical clamp device 10 can be formed of a metal material that can be reusable and sterilizable. However, a polymeric material (e.g., a molded polyethylene, polyvinyl chloride, polystyrene, or the like) that is either reusable and sterilizable or disposable for single use applications is also contemplated.

Figure 2:
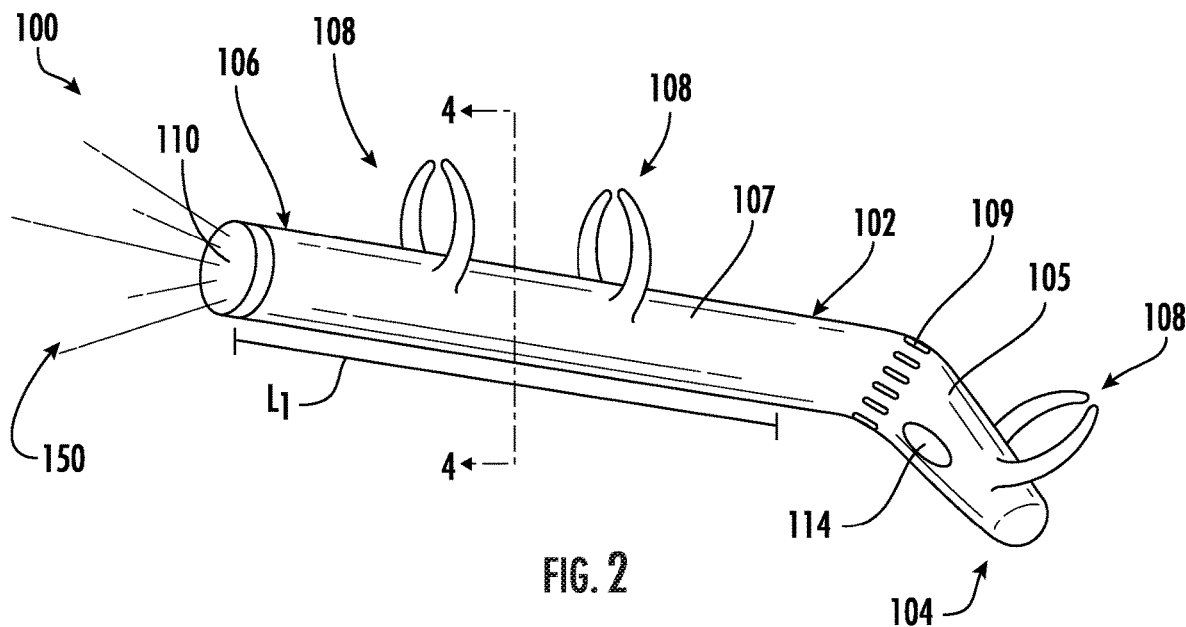
FIG. 2 illustrates a perspective view of the clamp light of FIG. 1.
Figure 3:
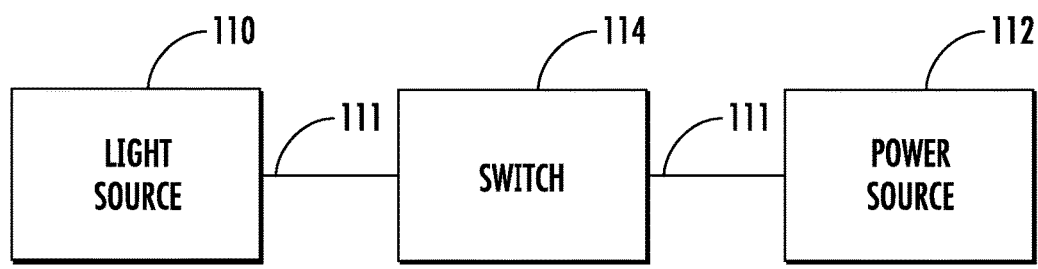
FIG. 3 illustrates a schematic diagram of the electrical components of the clamp light of FIG. 2.

As illustrated in FIGS. 1 and 2, the clamp light 100 of the present invention includes a housing 102 extending from a proximal end 104, which is configured to be positioned adjacent to the handle 12 of the medical clamp device 10 as shown in FIG. 1, to a distal end 106, which is configured to be positioned adjacent the elongated body 14 of the medical clamp device 10 towards the clamp 16 of the medical clamp device 10. The housing 102 can include a handle portion 105 extending from the proximal end 104 and configured to extend along the handle 12 of the medical clamp device 10. The housing 102 further includes an elongated portion 107 extending from the distal end 106 toward the handle portion 105. The elongated portion 107 is configured to extend along the elongated portion 14 of the medical clamp device 10 when the clamp light 100 is coupled to the medical clamp device 10 as shown in FIG. 1.

The overall shape of the housing 102 of the clamp light 100 is not particularly limited and can vary depending on the type of medical clamp device 10, e.g., alligator clamp or forceps, that are intended to be used with the clamp light 100 of the present invention. In general, the housing 102 is configured to have smaller dimensions than those of the medical clamp device 10. For instance, the elongated portion 107 has a length L1 that can be shorter than a length of the elongated portion 14 of the medical clamp device 10. Thus, the elongated portion 107 of the clamp light 100 is configured to avoid interfering with the at least one clamp 16 of the medical clamp device 10. In addition, the elongated portion 107 has a diameter D1 that can be less than or equal to a width or diameter of the elongated portion 14 of the medical clamp device 10 in order to avoid increasing the profile of the lighted clamp system 2 in the width direction when the clamp light 100 is coupled to the medical device 10.

In some embodiments, the housing 102 can include a flexible portion 109 disposed between the handle portion 105 and the elongated portion 107. The flexible portion 109 can be formed from a flexible polymer, an accordion-like angle-adjustable bellows segment, or other suitable flexible structure. The flexible portion 109 enables a user to adjust the angle between the handle portion 105 and the elongated portion 107. For example, the flexible portion 109 can be used to customize the angle between the handle portion 105 and the elongated portion 107 to couple to an angle between the handle 12 and elongated portion 14 of a medical clamp device 10. As the medical clamp devices 10 described by the present application may have varying shapes, angles, and lengths, the flexible portion 109 of the housing 102 importantly enables the clamp light 100 to be used with a variety of different medical clamp devices.

The housing 102 can be formed of any suitable medical grade material. In general, the housing 102 can be formed of a polymeric material (e.g., a molded polyethylene, polyvinyl chloride, polystyrene, or the like) that can be either disposable for single use applications or can be reusable and optionally sterilizable.

Figure 4:
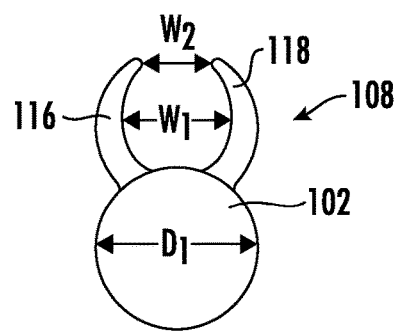
FIG. 4 illustrates a cutaway view of the clamp light of FIG. 2 taken along line 4-4 shown in FIG. 2.

The housing 102 further includes at least one attachment 108, e.g., a plurality of attachment clips 108 as shown in FIGS. 1 and 2. For instance, at least one attachment clip 108 can be located on the elongated portion 107 of the housing 102, and at least one attachment clip 108 can be located on the handle portion 105 of the housing, as shown in FIGS. 1 and 2. FIG. 4 illustrates a cutaway view of the housing 102 of the clamp light 100 taken along line 4-4 showing the profile of an attachment clip 108. Each attachment clip 108 includes a first arm 116 and a second arm 118 extending from the housing 102. The first and second arms 116 and 118 are separated by a width W1 adjacent to the housing 102 and a width W2 at the ends of the arms 116 and 118 distal from the housing 102. The width W1 can be equal to or wider than a width of the medical clamp device 10, e.g., a width of the elongate portion 14 of the medical clamp device 10, such that the medical clamp device 10 can be received between the first arm 116 and the second arm 118. Additionally, or alternatively, when the arms 116 and 118 are pliable, the width W1 may optionally be less than a width of the medical clamp device 10 prior to coupling the attachment 108 to the medical clamp device 10 and stretch or flex to receive the medical device 10 between the arms 116 and 118 when coupled. The width W2 can be less than or equal to a width of the medical clamp device 10, e.g., a width of the elongate portion 14 of the medical clamp device 10, prior to coupling the attachment 108 to the medical clamp device 10, such that the first arm 116 and the second arm 118 of the attachment 108 are configured to securely hold the medical clamp device 10 in place. In some embodiments, all or a portion of the first arm 116 and/or the second arm 118 can flex to allow a portion of the medical clamp device 10 to be placed through the opening at W2 in order to fit between the first arm 116 and the second arm 118 as shown in FIG. 1.

Although the attachment(s) 108 are illustrated as attachment clips having a first arm 116 and second arm 118, other types of attachments may be used in the present invention to couple the housing 102 of the clamp light 100 to a medical device 10. For instance, the at least one attachment 108 can be one or more of a screw, a bolt, a strap, an adhesive, e.g., a releasable adhesive or a permanent adhesive, a magnet, or other attachment mechanism. In an alternative embodiment, the housing 102 of the clamp light 100 can be integrally formed, e.g., molded, welded, or bonded (such as melt bonded, adhesively bonded, etc.), with the medical device 10 to form a lighted clamp system 2 that is integrally formed into a single unit.

As shown in FIGS. 1 and 2, the clamp light 100 includes a light source 110 disposed at the distal end 106 of the housing 102. The light source 110, when activated, illuminates an area 150 extending from the light source 110. For instance, when the clamp light 100 is coupled to a medical clamp device 10, as shown in FIG. 1, the area 150 illuminated by the light source 110 is configured to extend beyond the clamp 16 of the medical device clamp 10. The light source 110 can be any suitable type, and in one embodiment, can include at least one light emitting diode (LED). In general, the light source 110 can be designed to emit white light; however, emission of light of one or more colors may be contemplated, either by a different LED and/or by providing a cover at the distal tip 106 of the housing 102 over the light source 110.

In one embodiment, a light source 110 can deliver ultraviolet (UV) light to an area 150. UV light can be desirable in examination procedures in which a luminescent material is visualized. For instance, certain abnormal tissues can be visually detected by use of UV light. Diagnostic materials can also be detected by UV light. For instance, fluorescein solution can be applied to an area 150. Upon examination under UV light, tissue abnormalities can then be visually detectable. Such an embodiment can be used for the detection and/or visualization of tissues in a biopsy procedure. The clamp light 100 can be used with cervical biopsy forceps, tissue biopsy forceps, and/or specimen biopsy forceps for any such biopsy procedure. Moreover, the clamp light 100 can be used for biopsy procedures in veterinary medicine, or other applicable uses for the purpose of veterinary medicine.

The clamp light 100 further includes related electronics necessary for the light source 110 to emit light from the distal end 106 of the housing 102 in an area 150. The housing 102 contains the light source 110 and one or more electrical components, e.g., electrical connections 111 such as wires, a switch 114, and power source 112 necessary for proper function of the light source 110. The switch 114 can be in electrical communication with the light source 110 and can be a single-use switch or a multi-use switch. For instance, in those embodiments in which the clamp light 100 is a single-use, disposable device, the switch 114 can be a single-use switch, e.g., a tab formed of a non-conductive material. Upon removal of the tab, a circuit is closed between the power source 112 and the light source 110 will be powered to emit light in the area 150. However, any switch type may alternatively be utilized including, without limitation, a slide switch, a toggle switch, a button switch, etc.

The light source 110 can be in electrical connection with power supply 112, such as one or more batteries 112. The battery 112 can be contained within the housing 102, such as within the handle portion 105 of the housing 102. The size and type of the power source 112, e.g., one or more batteries, can vary as is known, generally depending upon the load expected and whether the device is intended to be a single-use or multi-use device. For instance, the clamp light 100 can include one or more 1.5V button-type batteries, e.g., disposable batteries, to power the light source 110.

In one embodiment, the light source 110 can be removable and replaceable. For instance, the light source 110 can be designed for replacement when a light emission device, e.g., a diode, becomes inoperable. In one embodiment, a device can allow replacement of a first light source, e.g., a white light emitting device, with a second light source, e.g., a UV emitting light. Thus, a device can be utilized for both visual inspection in standard conditions, e.g., with a white light, and for visual inspection using UV light, e.g., to visually detect a luminescent pathogen or detection solution. In yet another embodiment, the light source 110 can carry two different light emission devices, e.g., both a white LED emission source and a UV source. In this embodiment, the device can include electrical components, wires, switches, etc., examples of which are discussed further herein, that can allow the user to select which light emission is operating. Thus, during use the light emission in the area 150 can be modified as desired.

The clamp light 100 of the present invention is configured to be used with a medical clamp device 10, e.g., alligator forceps or clamp, or any tissue clamp sampling device, in a variety of medical procedures. For example, having the clamp light 100 coupled to a medical clamp device 10, as with the lighted clamp system 2 illustrated in FIG. 1, may be particularly useful for foreign body removal in tight body cavities; for instance, foreign body removal in the ear, e.g., ear wax, hearing aid, insect, or other foreign body removal from the ear canal. Additionally, the lighted clamp system 2 can be useful for foreign body removal from the vagina, such as removal of a tampon or other feminine hygiene article, condom, diaphragm, or other foreign body. Moreover, as described above, the lighted clamp system 2 can be used for visualization of tissue specimen in a biopsy procedure. In addition, the lighted clamp system 2 can be used for a variety of veterinary medicine procedures similar to the use of lighted clamp system 2 in medical procedures. The light source 110 of the clamp light 100 provides an illuminated area 150 beyond the clamp 16 of the medical clamp device 10, thereby providing enhanced, direct illumination of the path of the device 10. Thus, the lighted clamp system 2 helps a practitioner to avoid touching sensitive body wall tissues during a procedure (e.g., foreign body removal procedure) and can enable quicker and more accurate visualization and grasping of the foreign body. Furthermore, the lighted clamp system 2 having an illuminated area 150 surrounding the clamp 16 of the medical clamp device 10 can provide sufficient lighting to ensure there is no residual foreign material within the body cavity. As a result, foreign body removal procedures can be performed more quickly and accurately, which can result in greater patient satisfaction and can reduce the amount of anxiety experienced by a patient as a result of such procedure. Moreover, the use of the clamp light 100 during foreign body removal procedure can further reduce the time and personnel necessary for the procedure because a second practitioner is not required to hold or adjust a light source, such as a floor lamp, for the primary practitioner who is removing the foreign body from the patient's body cavity.

The clamp light 100 of the present invention can be a single-use device, e.g., disposable after a single use. When one or more batteries, e.g., 1.5V alkaline batteries, are used as the power source 112 for the light source 110 as described above, the alkaline batteries can be disposable and can require no special disposal precautions. The single-use clamp light 100 can be discarded in a standard sharps box following a procedure along with the instrument(s) used, e.g., medical clamp device 10.

It is to be understood that, while FIG. 1 contemplates coupling the clamp light 100 to a medical clamp device 10, the clamp light 100 may be coupled to and used in conjunction with any suitable medical device having a similar shape, e.g., elongated body and handle.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A disposable clamp light comprising:
a housing extending from a proximal end to a distal end, the housing comprising a handle portion and an elongated portion, an angle defined between the handle portion and the elongated portion, the handle portion extending from the proximal end towards the elongated portion, and the elongated portion extending from the distal end towards the handle portion;
a flexible portion disposed between the handle portion and the elongated portion, whereby the housing is configured to adjust the angle defined between the handle portion and the elongated portion;
a light source disposed at the distal end of the housing; and
at least one attachment configured to couple the disposable clamp light to a medical device.

2. The disposable clamp light of claim 1, further comprising a power source in electrical communication with the light source.

3. The disposable clamp light of claim 2, wherein the power source is a battery.

4. The disposable clamp light of claim 1, further comprising a switch in electrical communication with the light source.

5. The disposable clamp light of claim 4, wherein the switch is a single-use switch.

6. The disposable clamp light of claim 4, wherein the switch is a multi-use switch.

7. The disposable clamp light of claim 1, wherein the light source comprises at least one of a light emitting diode or an ultra-violet light emitting device.

8. The disposable clamp light of claim 1, wherein the housing comprises an upper surface extending from the proximal end to the distal end, wherein the upper surface of the housing is configured to be positioned adjacent to a lower surface of the medical device when the attachment is attached to the medical device, wherein a first portion of the upper surface of the housing is defined along the handle portion of the housing, the first portion of the upper surface of the housing configured to be positioned adjacent to a handle of the medical device, and wherein a second portion of the upper surface of the housing is defined along the elongated portion of the housing, the second portion of the upper surface of the housing configured to be positioned adjacent to an elongated body of the medical device.

9. The disposable clamp light of claim 1, wherein the at least one attachment comprises an attachment clip having a first arm and a second arm extending from the housing, wherein the first arm and the second arm are configured to surround a portion of the medical device to couple the disposable clamp light to the medical device.

10. The disposable clamp light of claim 1, wherein the at least one attachment comprises a plurality of attachments, the plurality of attachments comprising a first attachment extending from the handle portion of the housing and a second attachment extending from the elongated portion of the housing.

11. The disposable clamp light of claim 1, wherein the medical device is an alligator clamp, alligator forceps, or other foreign body removal device, the medical device having a handle, an elongated body, and at least one clamp for grasping an object.

12. A lighted clamp system comprising:
a clamp device comprising a handle, an elongated body, and at least one clamp for grasping an object; and
a disposable clamp light, wherein the disposable clamp light comprises a housing extending from a proximal end to a distal end, the housing comprising a handle portion adjacent to the handle of the clamp device and an elongated portion adjacent to the elongated body of the clamp device, an angle defined between the handle portion and the elongated portion, the handle portion extending from the proximal end towards the elongated portion and the elongated portion extending from the distal end towards the handle portion, a flexible portion disposed between the handle portion and the elongated portion, whereby the housing is configured to adjust the angle defined between the handle portion and the elongated portion, a light source disposed at the distal end of the housing, and at least one attachment; wherein the at least one attachment secures the disposable clamp light to the clamp device.

13. The lighted clamp system of claim 12, wherein the housing of the disposable clamp light comprises an upper surface extending from the proximal end to the distal end, wherein the upper surface of the housing is configured to be positioned adjacent to a lower surface of the clamp device, wherein a first portion of the upper surface of the housing is defined along the handle portion of the housing adjacent the handle of the clamp device and a second portion of the upper surface of the housing is defined along the elongated portion of the housing adjacent the elongated body of the clamp device.

14. The lighted clamp system of claim 12, wherein the housing of the disposable clamp light is integrally formed with the clamp device.

15. The lighted clamp system of claim 12, wherein the at least one attachment comprises an attachment clip having a first arm and a second arm extending from the housing, wherein the first arm and the second arm are configured to surround a portion of the clamp device to secure the disposable clamp light to the clamp device.

16. The lighted clamp system of claim 12, wherein the at least one attachment comprises a plurality of attachments.

17. The lighted clamp system of claim 12, wherein the clamp device is an alligator clamp, alligator forceps, or other foreign body removal device.

18. The lighted clamp system of claim 12, further comprising a power source in electrical communication with the light source.

19. The lighted clamp system of claim 18, wherein the power source is a battery.

20. The lighted clamp system of claim 12, further comprising a switch in electrical communication with the light source.

21. The lighted clamp system of claim 20, wherein the switch is a single-use switch.

22. The lighted clamp system of claim 20, wherein the switch is a multi-use switch.

* * * * *